United States Patent [19]
Chatterjee et al.

[11] Patent Number: 5,275,016
[45] Date of Patent: Jan. 4, 1994

[54] CRYOGENIC APPARATUS

[75] Inventors: Bikash K. Chatterjee, Fremont; Steven N. Buhl, Cupertino; Chi-Sou Yu, Saratoga; Thuy N. Tang, San Jose; Gary L. Smith, Walnut Creek; Bhaskar Bhayani, Fremont; Anthony Alvarado; Swee Wong, both of San Jose, all of Calif.

[73] Assignee: Abaxis, Inc., Sunnyvale, Calif.

[21] Appl. No.: 873,327

[22] Filed: Apr. 24, 1992

[51] Int. Cl.⁵ .................................... F25D 25/02
[52] U.S. Cl. ............................... 62/381; 2/78; 2/374
[58] Field of Search .............. 62/78, 63, 381, 48.1, 62/374

[56]           References Cited
             U.S. PATENT DOCUMENTS

| | | | |
|---|---|---|---|
| 2,166,915 | 7/1939 | Little | 62/48.1 |
| 2,214,009 | 9/1940 | Boester, Jr. | 62/101 |
| 2,835,477 | 5/1958 | Tovrog | 257/4 |
| 2,845,472 | 7/1958 | Narbutovskih | 174/15 |
| 3,228,838 | 1/1966 | Rinfret et al. | 62/78 |
| 3,282,064 | 11/1966 | Cowans | 62/45 |
| 4,256,576 | 3/1981 | Blickle | 62/538 |
| 4,261,183 | 4/1981 | Plomp | 62/381 |
| 4,386,504 | 6/1983 | Brautigam | 62/78 |
| 4,470,202 | 9/1984 | Buxton et al. | 34/5 |
| 4,594,226 | 6/1986 | Reedy | 422/89 |
| 4,760,712 | 8/1988 | Hashimoto | 62/381 |
| 4,798,614 | 1/1989 | Aubry | 62/374 |
| 4,848,094 | 7/1989 | Davis | 62/64 |
| 4,870,829 | 10/1989 | Oullette | 62/51.1 |
| 4,920,762 | 5/1990 | Beckstead | 62/353 |
| 4,982,577 | 1/1991 | Milankov | 62/381 |
| 4,989,416 | 2/1991 | Miller | 62/381 |

FOREIGN PATENT DOCUMENTS

| | | | |
|---|---|---|---|
| 20543/34 | 12/1934 | Australia | 29.7/83.1 |
| 2147880 | 3/1972 | Fed. Rep. of Germany | F25D 3/10 |
| 54-21643 | 2/1979 | Japan | F25D 3/10 |
| 14630 | 7/1903 | United Kingdom . | |

Primary Examiner—Ronald C. Capossela
Attorney, Agent, or Firm—Townsend and Townsend Khourie and Crew

[57]           ABSTRACT

The present invention provides methods and devices for freezing drops of liquid reagent solution in a cryogenic liquid. In one embodiment, the apparatus of the present invention comprises means for dispensing uniform, precisely measured drops of a liquid reagent and a rotatable carousel positioned below the dispensing means. The upper surface of the carousel has a plurality of trays each containing a cryogenic liquid, typically liquid nitrogen, for receiving the drops of liquid reagent. An alternative embodiment of the present invention comprises a tank comprising a cryogenic liquid for receiving the drops of liquid reagent. The tank has a heat source for slightly heating a portion of the cryogenic liquid such that a convection current in the cryogenic liquid is created. The convection currents in the cryogenic liquid provide mild agitation of the liquid and prevent aggregation of the frozen drops.

13 Claims, 2 Drawing Sheets

CRYOGENIC APPARATUS

BACKGROUND OF THE INVENTION

1. Field of the Invention

This invention relates to novel devices and methods for freezing drops of liquid reagent In particular, it relates to devices and methods for freezing liquid reagents useful in the analysis of biological samples.

In preparing reagents for convenient and efficient testing of clinical biological samples, it is frequently important to obtain dry chemical blends in uniform, discrete amounts. These reagents must be efficiently and economically prepared in small precisely measured quantities. Reagents comprising organic materials, however, tend to spoil or degrade on storage, thus creating quality control problems. Thus, reagents are typically provided in dried form to increase stability. This is preferably done by freezing and lyophilizing the aqueous solutions comprising the reagents to form reagent spheres.

2. Background Art

U.S. Pat. No. 4,848,084 relates to a method and apparatus for the generation of frozen droplets. Liquid is fed under pressure through a nozzle which provides a continuous stream of liquid which breaks apart to form droplets. The cryogenic liquid in the freezing tank is agitated with agitator 20. U.S. Pat. No. 4,982,577 discloses an apparatus and method for freezing droplets of liquid product. The apparatus uses cryogenic liquid, which flows along a ramp or sluiceway to freeze the droplets. U.S. Pat. No. 4,989,416 discloses an elongate tunnel which is inclined to the horizontal and which can be rotated along its longitudinal axis. Rotation of the tunnel carries the particles out of the liquid nitrogen contained therein. U.S. Pat. No. 4,798,614 relates to a freezing apparatus using a rotary chamber which rotates about a horizontal axis. U.S. Pat. No. 4,760,712 discloses a rotary chilling plate on which articles to be frozen are placed in brine. U.S. Pat. No. 4,920,762 discloses a method and apparatus for producing cryogenic targets using a mold assembly. U.S. Pat. No. 4,870,829 discloses a biological freezing apparatus containing a specimen holder which is lowered into a tank comprising a cryogenic liquid. U.S. Pat. No. 4,595,226 relates to a gas sample collection device which includes a specular carousel having at least one reflective surface for holding a sample deposited thereon.

U.S. Pat. No. 4,256,576 relates to a process for the creation of crystal aggregates in one part of the tank by heat transfer from a fluid disposed in another part of the tank. Both parts are separated from each other by a flexible membrane. U.S. Pat. No. 3,282,064 relates to cryogenic or refrigerant regeneration for use in closed cycle systems. U.S. Pat. No. 2,845,472 relates to an apparatus for cooling a transformer and means for recirculating the liquid coolant during the operation of the apparatus. U.S. Pat. No. 2,835,477 relates to an apparatus and method for controlling temperature in a bath. The temperature of the liquid bath is controlled by means of a temperature control conduit immersed in the bath through which the cooling liquid is circulated. U.S. Pat. No. 2,214,009 relates to an apparatus and method for cooling bottled beverages in which the cooling liquid is recirculated through a recirculation loop.

SUMMARY OF THE INVENTION

The invention relates to methods and devices for freezing drops of liquid reagent solutions in a cryogenic liquid. The apparatus of the present invention comprises means for dispensing uniform, precisely measured drops of a liquid reagent and a rotatable carousel positioned below the dispensing means. The upper surface of the carousel has a plurality of trays each containing a cryogenic liquid, typically liquid nitrogen, for receiving the drops of liquid reagent. Each tray preferably comprises a plurality of removable separators to facilitate the removal of the frozen drops. The separators and trays are preferably designed to be used directly in a lyophilizer.

The apparatus also contains means for rotating the carousel about its vertical axis. The apparatus preferably comprises means for coordinating the rotation of the carousel with the dispensing of the drops, typically a photosensor.

The dispensing means preferably comprises a nozzle tip, through which the liquid is dispensed, a cowling around the nozzle tip and a gas port for blowing gas along the nozzle tip thereby preventing moisture condensation on the nozzle tip.

The liquid reagent solution preferably comprises a reagent useful for the analysis of a biological sample, such as blood. To ensure that the resulting lyophilized reagent spheres are uniform in size, the apparatus of the invention preferably includes means for degassing the liquid reagent solution before dispensing.

An alternative embodiment of the present invention comprises means for dispensing uniform, precisely measured drops of the liquid reagent and a tank comprising a cryogenic liquid for receiving the drops of liquid reagent. The tank has a heat source (e.g., a heater coil) for slightly heating a portion of the cryogenic liquid such that a convection current in the cryogenic liquid is created. The convection currents in the cryogenic liquid provide mild agitation of the liquid and prevent aggregation of the frozen drops. The dispensing means in this embodiment are as described above.

The insulated tank may comprise a recirculation loop on which the heating coil is placed. Alternatively, the heating coil may be placed in the tank, itself.

DESCRIPTION OF THE PREFERRED EMBODIMENT

Figure 1:
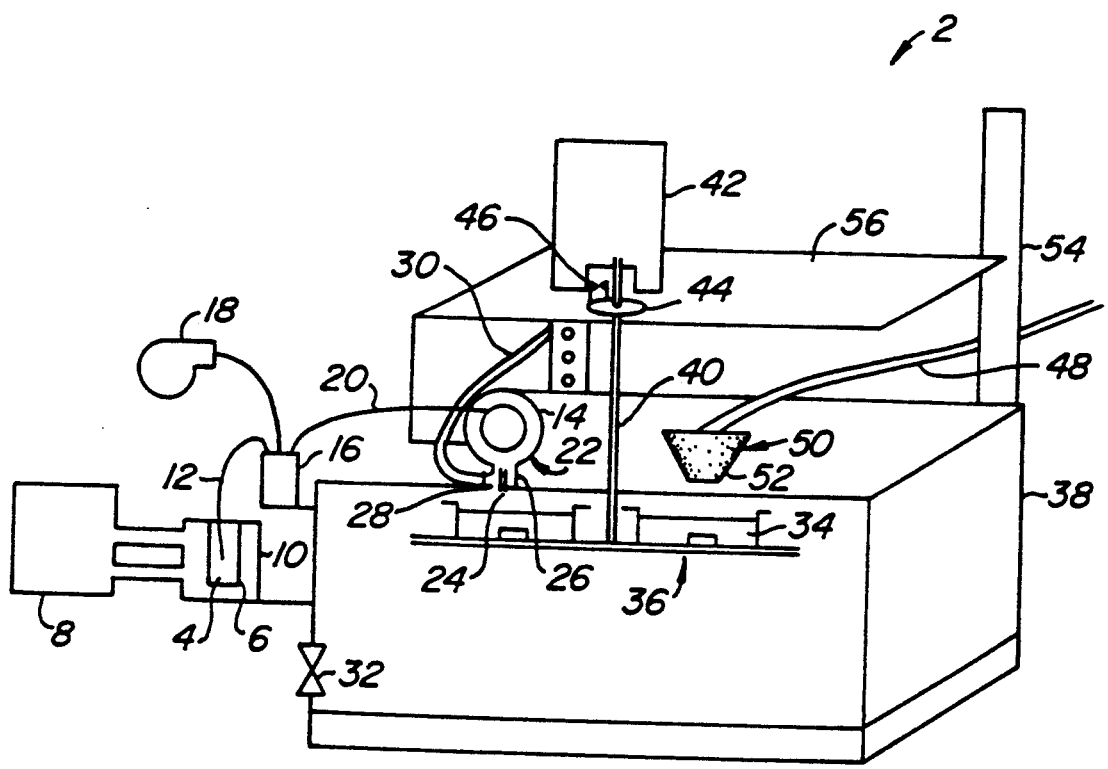
FIG. 1 is a perspective view of one embodiment of the present invention.

The present invention provides devices and methods for producing lyophilized reagent spheres useful in analyzing biological samples, such as blood plasma or serum, in centrifugal analyzers. The reagent spheres are prepared from reagents suitable for any of a number of analytical assays of biological samples.

The lyophilized reagent spheres produced by the devices and methods of the present invention are suitable for use in centrifugal analyzers for optically analyzing biological fluids, in particular blood plasma or serum. Centrifugal rotors used in such analyzers typically comprise means for mixing the blood with an appropriate diluent and separating plasma from cellular material. The rotors also provide for distribution of the diluted plasma into a plurality of cuvettes within the rotor so that different optical analytic procedures may be performed without having to transfer aliquots of the fluid from the apparatus. One or more reagent spheres comprising the reagents necessary for a desired assay are provided in each cuvette.

The rotors and methods described in the following U.S. patents are preferably used: U.S. Pat. No. 5,061,381; 5,173,193; 5,122,284 and 5,186,844. The entire disclosure of these applications are incorporated herein by reference. The above applications disclose centrifugal rotors for separating plasma from whole blood that include a plurality of internal chambers and passages for combining blood plasma or serum with one or more reagents and distributing the plasma or serum to a plurality of individual test wells. The chambers and passages necessary for separating the whole blood into plasma are located radially outward from metering chambers that deliver precisely measured volumes of blood and/or diluent to a separation chamber. The separation chamber includes a radially-outward cell trap. Spinning of the rotor causes the cellular components of the whole blood to be sequestered in the cell trap. The separated plasma is then delivered to a plurality of test wells or cuvettes. The above separation and aliquoting steps typically occur as a result of centrifugal force generated by the spinning rotor.

The compositions of the present invention in combination with the rotors described above are particularly suitable for analyzing blood plasma or diluted blood plasma. They are also useful with a wide variety of other biological fluids, such as urine, sputum, semen, saliva, ocular lens fluid, cerebral fluid, spinal fluid, amniotic fluid, and tissue culture media, as well as food and industrial chemicals, and the like.

The compositions of the present invention are particularly suitable for performing a wide variety of analytic procedures which are beneficially or necessarily performed on blood plasma or diluted plasma. The analytic procedures will generally require that the blood plasma be combined with one or more reagents so that some optically detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and do not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, alkaline phosphatase, c-reactive protein bilirubin, calcium, chloride, sodium, potassium, magnesium, and the like. This list is not exhaustive and is intended merely as being exemplary of the assays which may be performed using the apparatus and method of the present invention. Usually, these tests will require that the blood plasma be combined with one or more reagents which result in a visually detectable, usually photometrically detectable, change in the plasma. Suitable reagent solutions are disclosed in copending application U.S. Ser. No. 07/747,179, which is incorporated herein by reference.

The lyophilized reagent spheres of the present invention dissolve quickly in an aqueous sample solution, or diluent. A sample solution of the present invention may be a diluted or undiluted biological sample. The reagent spheres typically dissolve in less than about 30 seconds, preferably less than about 10 seconds. The rapidity of dissolution gives the impression that the reagent sphere "explodes" and distributes the dissolving chemicals throughout the reconstituting volume. Rapid dissolution of the spheres is facilitated by a chemical lattice structure which quickly conducts water into the reagent sphere. To form the chemical lattice, fillers are included in the aqueous solution used to produce the spheres. As the reagent spheres are lyophilized, these molecules facilitate formation of a network of open spaces or a chemical lattice in the spheres. The filler components of the reagent spheres are typically polymeric compounds, such as bovine serum albumin, polyethylene glycol, dextran, Ficoll ® (Pharmacia LKB Biotechnology, Inc., Piscataway, N.J.), or polyvinylpyrrolidone. In addition, emulsifiers such as sodium cholate and the like are useful as fillers. Monosaccharides and their derivatives, such as mannitol or the polyalcohol, myo-inositol, can also be used. Depending upon the assay, the fillers can be used individually or in combination with one or more of the other filler components.

In addition to fillers, the reagent spheres of the present invention also comprise one or more surfactants at concentrations sufficient to inhibit bubble formation when the spheres are rapidly rehydrated. As described above, bubbles are detrimental to the assays because they interfere with optical measurements. If the reagent spheres comprise surfactants at the appropriate concentrations, however, such problems are avoided. Suitable surfactants include non-ionic detergents such as polyoxyethylene 9 lauryl ether, octoxynol 9, Synthrapol ®, NP-90, Trycol ® 5941, Trycol ® 6735 and the like. Ionic detergents such as Gafac ® 560, sodium dodecyl sulfate and the like are also suitable. Typically, the surfactants are present in the reconstituted reagent spheres at a concentration between about 0.08 g and about 3.1 g per 100 ml. The surfactant concentration used will depend upon the particular reagents used in the assay.

The fillers and surfactants used in a particular reagent sphere preparation are preferably selected so as to minimize interference with the assay. In addition, to provide reagent spheres of the correct size in a test well, the components are typically concentrated in the reagent sphere. Upon rehydration with a predetermined volume of sample, the reagents and other components are present in the correct concentration. For instance, the components of the reagent spheres for alkaline phosphate determinations are typically at about 6×concentration and total protein reagents are at about 2.7×concentration. The ideal concentration for the reagents for particular assay can be easily determined, depending upon size of the test well, sample volume, and the like.

The reagent spheres produced by the apparatus of the present invention are prepared from reagents suitable for any of the analytical assays discussed above. Typically, an aqueous solution comprising the reagents is prepared. To ensure uniform composition of the reagent spheres, the solution must be homogeneous and all constituents must be fully dissolved or in suspension. The devices of the present invention are then used to dispense individual drops of the solution into a carousel or insulated tank comprising cryogenic liquid, preferably liquid nitrogen. A cryogenic liquid as used herein refers to a liquified gas having a normal boiling point below about −75° C., preferably below about −150° C.

The frozen masses are then removed from the cryogenic liquid and lyophilized to produce the reagent spheres. The reagent spheres typically comprise less than about 6% residual moisture, preferably less than about 3%. Lyophilization is carried out according to standard procedures known in the art. Typically, the frozen drops are lyophilized for about 4 hours to about 24 hours at about 50 to about 450 mTorr, preferably, about 6 hours at about 200 mTorr.

The drops are uniform and precisely measured so that the resulting dried reagent spheres have uniform mass. The uniformity of the reagent spheres obviates the need for an additional tableting step to obtain uniform size. When the drops are uniform and precisely measured, the imprecision of the mass (coefficient of weight variation) of the reagent spheres prepared from the drops is less than about 3%, and preferably between about 0.3% and about 2.5%. To further decrease the coefficient of weight variation, the aqueous solution is preferably degassed using a vacuum pump or vacuum line before the drops of solution are dispensed.

To obtain values for coefficient of weight variation, known quantities of reagent spheres are weighed. The coefficient of variation (C.V.) is then determined as follows:

$$C.V. = J/\bar{x} \times 100$$

wherein
wherein
J = standard deviation (for n sphere) =

$$\left[ \frac{(x - \bar{x})^2}{n - 1} \right]^{\frac{1}{2}}$$

x = weight of one sphere
$\bar{x}$ = (for "n" sphere) = $\Sigma x/n$

The devices of the present invention comprise dispensing means which provide the precision necessary to produce uniform drops. A high precision pump is used to pump the liquid through the dispensing means. The pump should be of a design which minimizes shear and heat generation in the pump head. Typically, an IVEK model AAA pump (N. Springfield, Vt.) is used to pump the liquid reagent solution through the dispensing means. The pump system should also be of a design to allow control of the pump rate, dispensing volume, fluid drawback in the line and dispensing frequency. The term "pump rate" applies to the speed with which the pump motor opens and closes the pump cavity. The term "drawback" refers to the distance the fluid meniscus at the outlet of the dispensing means, moves back during the pump cycle. The drops are typically dispensed with a frequency ranging from 1 to 3 drops per second and usually dispensed with a frequency of 1 to 2 drops per second. There is no lower limit to dispensing frequency.

For instance, in preparing reagent spheres for total protein determinations, 2.96 μl drops are typically used, for C-reactive protein and alkaline phosphatase determinations, 2.67 μl are used. Volumes appropriate for other tests are as follows: SGOT, 4.0 μl; potassium, 4.0 μl; creatinine, 4.0 μl; bilirubin, 2.667 μl; amylase, 2.667 μl; cholesterol, 2.667 μl; uric acid, 3.478 μl; and glucose, 2.065 μl.

The dispensing means of the present invention also comprises a nozzle tip designed to provide substantially uniform drop size. A variety of nozzle tips can be used so long as sufficient uniformity of drop size is provided. The nozzle tips are typically made of Trifluoroethylene or some other polymer with equivalent rigidity and surface characteristics. The size of the orifice in the nozzle tip will depend upon the composition of the liquid reagent and the operating pressure used to pump the reagent. Typically, the inside diameter of the orifice in the nozzle tip is between 0.020 and 0.040 inches, usually between about 0.027 and 0.035 inches, and preferably between about 0.029 and 0.031 inches. The nozzle tip is typically tapered and has a tip wall thickness ranging from 0.005 inches to 0.016 inches depending upon the properties of the liquid reagent being dispensed.

The dispensing means is preferably positioned a sufficient distance above the cryogenic liquid surface to permit the fluid drop to form a sphere before it lands on the surface of the cryogenic liquid. However, spacing the dispensing means too great a distance above the cryogenic liquid permits the drop to break up into droplets prior to contacting the cryogenic liquid. The dispensing means is typically positioned between about 8 cm and 13 cm above the cryogenic liquid, preferably about 10 cm. The precise distance used will depend upon the particular design of the apparatus and the design of the dispensing means used. This distance can be determined by minimal experimentation once other design variables are specified. Alternately, the dispensing means may be oriented such that the reagent drops follow a trajectory which allows them to impact the surface of the cryogenic liquid with a velocity near zero cm/sec. This typically will require the dispensing means to be oriented 0°–180° to the cryogenic liquid surface.

In one embodiment of the present invention, the cryogenic liquid is contained within trays placed on a rotatable carousel. Each tray is divided into subsections using removable separators. The carousel rotates about its vertical axis so that each tray is successively rotated under the dispensing means. The drops are separated by the removable separators after dispensing. This provides each bead with the same exposure time to the cryogenic liquid (dwell time) and ensures that the beads will have completely frozen and sunk below the surface of the liquid before dispensing the next drop of reagent into the same area. This prevents the formation of double beads, i.e. beads which have stuck together during freezing. The velocity of the rotating carousel is selected such that no movement to the cryogenic liquid is imparted, thereby maintaining the smooth surface for dispensing.

In an alternate embodiment, the cryogenic liquid is contained within an insulated tank. To prevent aggregation of the frozen liquid reagent drops, movement of the liquid nitrogen is created by the use of a heater which raises the temperature of a portion of the cryogenic liquid slightly. Convection currents are created as a result of the movement of fluid caused by the density differences between the heated and unheated portions of the liquid. The heating of the portion of the cryogenic liquid is selected so as to avoid excessive agitation of the liquid as a result of boiling. Typically, the temperature differential between the heated and unheated cryogenic liquid will be greater than 50° C. The heater should span the width of the insulated tank.

An alternate method for creating the appropriate movement in the cryogenic liquid is by placing dry nitrogen jets near the surface of the liquid nitrogen. As the gas is expelled from the nozzles velocity is imparted to the surface of the cryogenic liquid and movement is created.

The tank in either of the above two embodiments utilizes the movement of the cryogenic liquid to direct the frozen reagent beads to an area of the tank where a perforated plate or screen is used to capture the frozen reagent beads. This screen can then be removed and the beads transferred to a tray for lyophilization.

Referring now to FIGS. 1-4, the cryogenic apparatus 2 constructed in accordance with the principles of the present invention will be described in detail. A liquid reagent solution 4 is held in reservoir 6 where it is kept at an appropriate temperature via recirculating water bath 8 and jacket 10. The temperature of the water in the jacket ranges from room temperature to 4° C. depending upon the reagent properties. The temperature of the reagent liquid effects the viscosity of the reagent liquid which in turn effects the overall dispensing precision. The liquid reagent is drawn through line 12 by the dispensing pump 14 and delivered to the degassing chamber 16. The solution is degassed for about 29 minutes using vacuum pump 18. The solution is then drawn through line 20 to the dispensing means 22.

The dispensing means 22 comprises nozzle tip 24 surrounded by cowling 26. A dry nitrogen dispensing tip 28 supplies dry nitrogen from dry nitrogen tubing 30 and creates a microenvironment around the nozzle tip which prevents moisture from condensing and the tip from freezing. The dry nitrogen gas also creates a positive pressure which preferentially redirects any cryogenic liquid vapor away from the nozzle tip and towards an exhaust port 32. The dry nitrogen is typically supplied at a pressure of between 10 and 15 pounds per square inch (psi).

Liquid reagent 4 dispensed from the dispensing means 22 is received by the cryogenic liquid 34 contained in the carousel 36 positioned below the dispensing mean 22. The carousel 36 is rotatably mounted in the insulated tank 38 and is rotated about carousel spindle 40 positioned at the vertical axis of rotation of the carousel 36. The spindle 40 is connected to a motor 42 which drives the rotation of the carousel. The carousel is usually rotated at between about 4 and 10 rpm. The preferred range is between about 4 and 6 rpm.

The carousel spindle 40 comprises a photosensor trigger 44 which is detected by photosensor 46 to allow coordination of the rotation of the spindle with the rate of dispensing of drops of liquid reagent by the dispensing means 22. Specifically, the trigger 44 has a number of pegs (not shown) projecting radially from its outer edge which act as optical triggers for the photosensor 46. The photosensor 46 is a standard photosensor well known to those skilled in the art. It typically includes a reflective photo-emitter detector module which furnishes a light source and a phototransistor to determine if light has been reflected off of a predetermined surface. A conditioning circuit is used to bias the electro-optical module to control length of time for the dispense pump. A driver is used to control a relay which isolates the control circuit from the dispensing mechanism.

Cryogenic liquid (typically liquid nitrogen) is supplied through supply line 48 and is dispensed through cryogenic liquid dispensing means 50. This dispensing means includes a protective cowling 52. The insulated tank 38 is supported by tank support frame 54 and the motor 42 is positioned on the motor support shelf 56.

Figure 2:
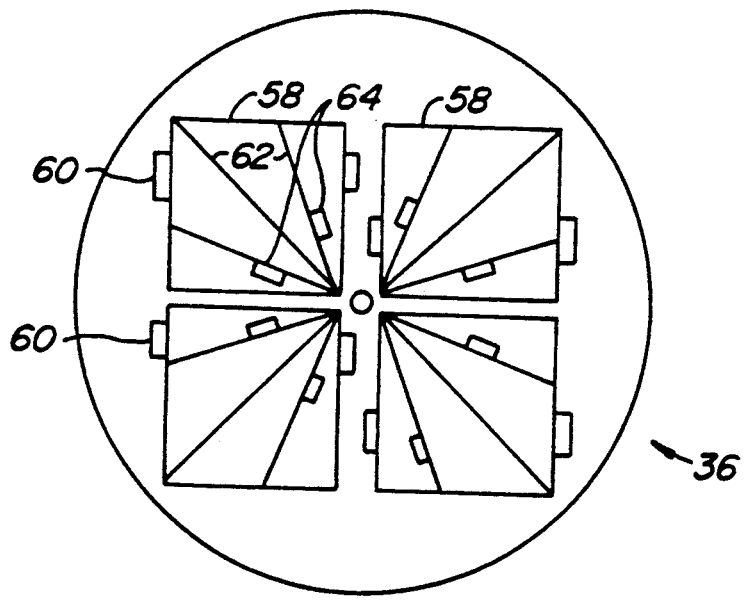
FIG. 2 is a top plan view of a carousel of the present invention.

The carousel of the present invention is seen more clearly in FIG. 2. The carousel is shown here as a circular disc. It will be understood, however, that other shapes (e.g., rectangular) may also be used. The carousel 36 comprises four dispensing trays 58, which each comprise a tab 60 to facilitate removal of the trays 58 from the carousel 36. Each tray 58 is subdivided by separators 62 which also comprise separator tabs 64 to facilitate removal of the separators 62 from the trays 58. The rate of dispensing of liquid reagent is a function of the size of the trays 58 in the carousel, the rate of rotation and the number of separators 62. These parameters are adjusted to ensure the appropriate dwell time of the bead before sinking below the surface of the cryogenic liquid. After each tray 58 receives the desired number of liquid drops, it is removed and replaced with another tray. After completion of dispensing, the trays 58 and their separators 62 are removed and put directly into the lyophilizer.

Figure 3:
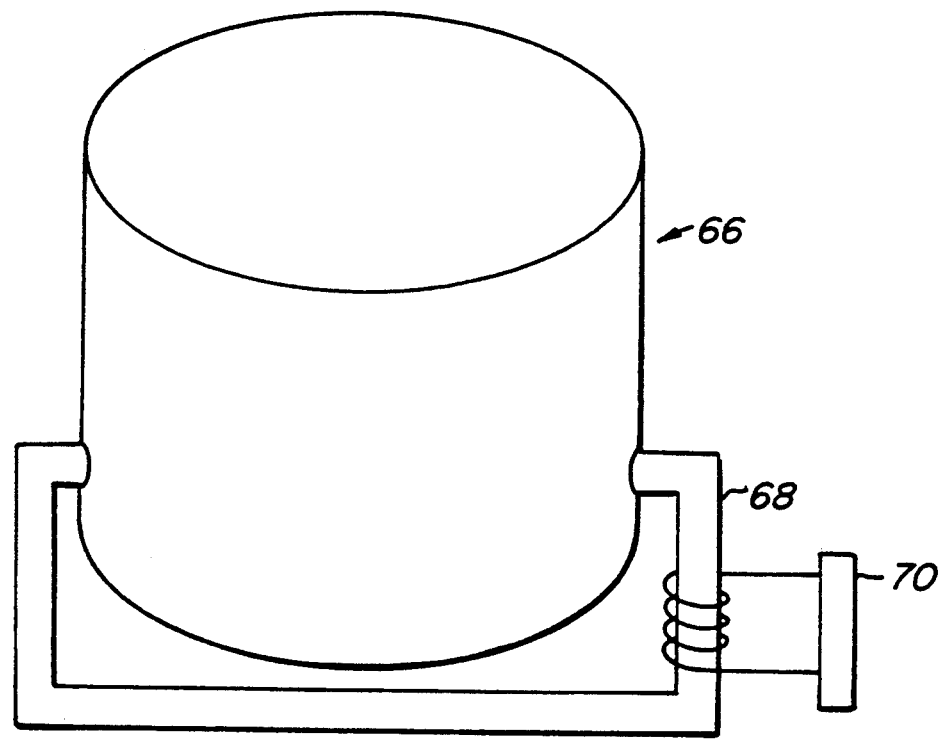
FIG. 3 is a perspective view of an embodiment of the present invention in which cryogenic liquid is heated in a recirculation loop.
Figure 4:
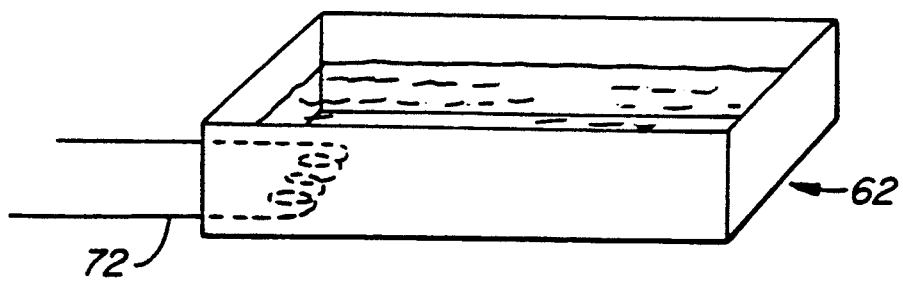
FIG. 4 is a perspective view of an embodiment of the present invention in which a portion of the cryogenic liquid is heated in the tank.

Turning now to FIG. 3, the cryogenic liquid tank 66 of the present invention utilizing a heater coil to create convection currents and thereby create movement in the cryogenic liquid is illustrated. Although not shown here, the cryogenic liquid tank 66 is typically positioned below a dispensing means as described in FIG. 1. The cryogenic liquid tank 66 comprises a recirculation loop 68 on which is positioned a heater coil 70. In operation, the heater coil is used to heat the cryogenic liquid slightly. This creates convection currents within the recirculation loop. The convection currents then create movement of the cryogenic liquid within the tank 66 which move the dispensed liquid reagent drops away from the dispensing area, allowing them to freeze and sink below the surface of the liquid. FIG. 4 presents an alternate embodiment of a cryogenic liquid tank 66 of the present invention. In this embodiment, a heat source 70 is placed within the tank, itself and thereby creates temperature differentials within the cryogenic liquid.

Although the foregoing invention has been described in detail for purposes of clarity of understanding, it will be obvious that certain modifications may be practiced within the scope of the appended claims.

What is claimed is:

1. A cryogenic carousel apparatus comprising:
    means for dispensing uniform, precisely measured drops of a liquid reagent;
    a rotatable carousel having a vertical axis of rotation, the carousel being positioned to receive reagent drops from the dispensing means and comprising a plurality of trays each containing a cryogenic liquid for receiving the drops of liquid reagent;
    means for conveying cryogenic liquid to each tray; and
    means for rotating the carousel about the vertical axis.

2. The cryogenic apparatus of claim 1, wherein each tray comprises a plurality of removable separators.

3. The cryogenic apparatus of claim 1, wherein the cryogenic liquid is liquid nitrogen.

4. The cryogenic apparatus of claim 1, further comprising means for degassing the liquid reagent.

5. The cryogenic apparatus of claim 1, wherein the carousel is disposed within an insulated tank.

6. The cryogenic apparatus of claim 1, wherein the means for dispensing comprises a nozzle tip, through which the liquid is dispensed, a cowling around the nozzle tip and a gas port for blowing gas along the nozzle tip thereby preventing moisture condensation on the nozzle tip.

7. The cryogenic apparatus of claim 6, wherein the gas is nitrogen.

8. The cryogenic apparatus of claim 1, further comprising means for coordinating the rotation of the carousel with the dispensing of drops of liquid reagent.

9. The cryogenic apparatus of claim 8, wherein the means for coordinating the rotation of the carousel comprises a photo sensor.

10. A cryogenic apparatus comprising a
    means for dispensing uniform, precisely measured drops of a liquid reagent;
    a tank comprising a cryogenic liquid for receiving the drops of liquid reagent, the tank being disposed to receive the reagent drops from the means for dispensing and having a heat source for slightly heating a portion of the cryogenic liquid such that a convection current in the cryogenic liquid is created and means for conveying cryogenic liquid to the tank.

11. The cryogenic apparatus of claim 10, further comprising a recirculation loop connected to the tank on which recirculation loop the heat source is disposed.

12. The cryogenic apparatus of claim 10, wherein the cryogenic liquid is liquid nitrogen.

13. The cryogenic apparatus of claim 10, wherein the means for dispensing comprises a nozzle tip, through which the liquid is dispensed, a cowling around the nozzle tip and a gas port for blowing gas along the nozzle tip thereby preventing moisture condensation on the nozzle tip.

* * * * *